United States Patent
Colatsky et al.

[11] Patent Number: 4,665,227
[45] Date of Patent: May 12, 1987

[54] N-SUBSTITUTED-4(3)-NITROBENZENE SULPHONAMIDES

[75] Inventors: Thomas J. Colatsky, Paoli; George C. Buzby, Jr., Blue Bell, both of Pa.

[73] Assignee: American Home Products Corporation, New York, N.Y.

[21] Appl. No.: 867,348

[22] Filed: May 23, 1986

[51] Int. Cl.$^4$ .................................... C07C 143/78
[52] U.S. Cl. .................................... 564/87
[58] Field of Search .................................... 564/87

[56] References Cited

U.S. PATENT DOCUMENTS

| | | | |
|---|---|---|---|
| 2,233,296 | 2/1941 | Nelles et al. | 564/92 |
| 3,580,949 | 5/1971 | Gruenman et al. | 260/370.5 |
| 3,687,870 | 8/1972 | Muzyczko et al. | 564/87 |

FOREIGN PATENT DOCUMENTS

| | | |
|---|---|---|
| 1912848 | 10/1969 | Fed. Rep. of Germany . |
| 47-37413 | 9/1972 | Japan . |
| 1053204 | 12/1966 | United Kingdom . |

OTHER PUBLICATIONS

Silberg et al., ACAD Rep Populace Romire, Fillala Clug, Studee Cercetari Med., 10 241-252 (1959).
Bexton et al., Pharmac. Ther. 17, 315-55 (1982).
Vaughan-Williams, J. Clin. Pharmacol. 24, 129-47 (1984).
Thomis et al., Ann. Rep. Med. Chem. 18, 99-108 (1983).
Fleckenstein, Ann. Rev. Pharmacol., 17 149-66 (1977).

Primary Examiner—Anton H. Sutto
Attorney, Agent, or Firm—Richard K. Jackson

[57] ABSTRACT

Compounds presenting the following structural formula:

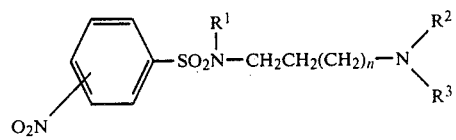

in which the nitro substituent is in 3 or 4 position of the phenyl ring;
$R^1$ is hydrogen or alkyl;
$R^2$ is alkyl;
$R^3$ is hydrogen or alkyl;
and n is one of the integers 0, 1 or 2;
or a pharmaceutically acceptable salt thereof, are Class III anti-arrhythmic agents.

12 Claims, No Drawings

N-SUBSTITUTED-4(3)-NITROBENZENE SULPHONAMIDES

BACKGROUND OF THE INVENTION

Class III anti-arrhythmic agents may be categorized as having the ability to markedly prolong cardiac action potential duration without producing significant changes in maximal upstroke velocity. Unlike Class I anti-arrhythmic agents, a pure Class III agent displays no effects on cardiac sodium channels. The electrophysiologic properties of a compound defining a Class III activity profile are observed in vivo as negligible effects on atrial, ventricular and H-V conduction time while producing a marked increase (greater than 20 percent) in both the atrial and ventricular refractory period. In contrast, Class I agents will demonstrate a marked slowing of ventricular conduction velocity without significant changes in ventricular refractory period. Recent reviews of these agents are by Bexton et al., Pharmac. Ther. 17, 315–55 (1982); Vaughon-Williams, J. Clin. Pharmacol. 24, 129–47 (1984) and Thomis et al., Ann. Rep. Med. Chem. 18, 99–108 (1983).

DESCRIPTION OF THE INVENTION

In accordance with this invention there is provided a group of anti-arrhythmic agents of the formula:

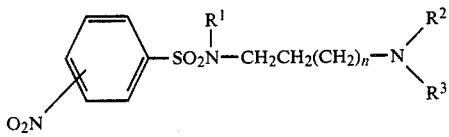

in which
the nitro substituent is in 3 or 4 position of the phenyl ring;
$R^1$ is hydrogen or alkyl of 1 to 4 carbon atoms;
$R^2$ is alkyl of 1 to 4 carbon atoms;
$R^3$ is hydrogen or alkyl of 1 to 4 carbon atoms;
and n is one of the integers 0, 1 or 2;
or a pharmaceutically acceptable salt thereof.

Among the compounds of the above-described genus there resides a group of preferred compounds which possess a superior Class III anti-arrhythmic activity profile. These preferred compounds are of the structural formula:

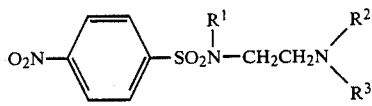

in which
$R^1$ is hydrogen or branched chain alkyl of 3 or 4 carbon atoms;
$R^2$ is branched chain alkyl of 3 or 4 carbon atoms;
$R^3$ is hydrogen or branched chain alkyl of 3 or 4 carbon atoms;
or a pharmaceutically acceptable salt thereof.

The pharmaceutically acceptable salts of the anti-arrhythmic agents of this invention are prepared directly by neutralization of the free base. These physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicyclic, lactic, naphthalenesulfonic acid, and the like.

The compounds of this invention are prepared by reaction of a nitro substituted benzene sulfonyl halide with an appropriately substitued α,ω-alkane diamine of 2 to 4 carbon atoms. These reactants are generally known compounds and otherwise are routinely prepared by techniques well within the skill of the chemist.

The compounds of this invention demonstrate anti-arrhythmic activity when tested in the standard experimental animal in accordance with the following procedure:

Rats weighing between 400–500 gms were anesthetized with 35–40 mg/kg sodium pentobarbital intraperitoneally. Rats were close-clipped on the neck and left thorax prior to cannulation of the jugular vein and carotid artery for measurement of arterial blood pressure and injection of drug. A tracheotomy is performed and respiration provided by a Harvard Model 681 respirator at a rate of approximately 55 min and a volume of 4 cc per cycle. The rat was then placed upon its right side and the heart was exposed by making an incision and separating the ribs. 4-0 Silk on taper RB-1 needle was passed under the left anterior descending coronary artery (LAD) at a location just under the tip of the left atrial appendage. The suture was left to be tied upon occlusion.

The rat was allowed to stabilize for 5 to 15 minutes before the administration of drug as a bolus via the cannulated jugular vein. The total drug dose volume is kept constant between 0.20–0.25 ml. Fifteen minutes after dosing, the LAD was occluded by tying the suture. This procedure provokes severe ventricular arrhythmias, terminating in ventricular fibrillation and death in at least about 65 percent of animals given vehicle only. The development and progression of ventricular arrhythmia is monitored for a period of 20 minutes. Lead II ECG and cardiotachometer output were recorded on a Beckman R612 recorder.

Mean arterial pressure (MAP) is monitored throughout the experiment, and the following values recorded: (1) MAP prior to drug, (2) maximal change in MAP following drug and before LAD occlusion, and (3) MAP just prior to LAD occlusion. Changes in cardiac electrical activity are determined from the Lead II electrocardiogram. The dysrhythmias are scored as follows: (1) normal sinus rhythm, (2) isolated premature ventricular complexes, (3) non-sustained ventricular tachycardia (repetitive beats of ventricular origin lasting ≦15 sec.), (4) sustained ventricular tachycardia (repetitive ventricular activitiy lasting ≧15 sec.), (5) self-terminating or reversible ventricular fibrillation (VFrev), and (6) irreversible VF (VF irrev. death). The incidence of death in the drug-treated group is then compared to that in the untreated control group (generally ≧65%). Five animals are included in each drug group.

Arrhythmias scores are calculated for each group of animals for purposes of obtaining more quantitative rankings for anti-arrhythmic efficacy. The equation, $$\sum_{n=1}^{i} A \times AS,$$

is used, where A=fraction of animals with a certain kind of arrhythmia (e.g., ventricular fibrillation, sustained ventricular tachycardia) and AS is the arbitrary score assigned to that arrhythmia:

|     | A                                        | AS  |
| --- | ---------------------------------------- | --- |
| (a) | no arrhythmia                            | −5  |
| (b) | isolated premature beats (PVC's)         | +5  |
| (c) | non-sustained ventricular tachycardia    | +10 |
| (d) | sustained ventricular tachycardia        | +20 |
| (e) | reversible ventricular fibrillation      | +40 |
| (f) | death                                    | +50 |

Thus, for the purpose of these coronary ligation (C.L.) experiments, a score from −5 (no arrhythmia) to 50 (death) is assigned to the response of each rat in a test group, based upon the number, type and severity of each response. The sum of the percent of animals at each response level times the point score assigned that response level equals the score value of the compound being tested. The lower the score, the more active the compound in preventing ventricular dysrhythmia.

To further characterize the anti-arrhythmic activity of the compounds of this invention, they were tested in accordance with the following standard test procedure:

Bundles of free-running Purkinje fibers with attached myocardium obtained from either ventricle of adult dog heart were pinned without stretching to the bottom of a 10 ml tissue chamber and continuously superfused with oxygenated Tyrode's solution at a flow rate of 10 ml/min. The composition of the Tyrode's solution was (mM): NaCl 150; KCl 4.0; $CaCl_2$ 2.7; $MgCl_2$ 0.5; HEPE buffer (7.4) 10; dextrose 5.5. The solution was aerated with 100% $O_2$. Bath temperature was maintained at 36±0.5° C. by circulating the superfusate through a thermostatically controlled water bath immediately prior to entering the tissue chamber.

Preparations were stimulated through bipolar Teflon-coated platinum wires, bared at the tips, placed on the endocardial surface of the attached myocardium using a W.P.I. digital stimulator set to deliver constant current pulses 1-2 msec in duration at cycle lengths (c.l.) of 330 or 1000 msec. Stimulus strength was set at approximately 2× diastolic threshold, and adjusted as required throughout the experiment. All preparations were allowed to equilibrate in the tissue chamber for at least 1 hour before measurements were begun. Subsequently, a minimum of 60 minutes was allowed for equilibration with each drug-containing superfusate before post-drug measurements were made. Impalements were made at 6-10 sites throughout the preparation before and after drug exposure. Offset potentials were re-checked at the conclusion of each experiment.

Glass microelectrodes filled with 3M KCl were coupled to high impedance negative capacitance electrometers (W. P. Instruments, New Haven, CT), and Ag/AgCl half-cells used as reference electrodes. The first derivative of the action potential upstroke ($\dot{V}max$) was obtained using an analog differentiator circuit, coupled to a peak-hold circuit that retained the recorded value of $\dot{V}max$ for 30-70 msec. Action potential and $\dot{V}max$ tracings were displayed on a Tektronix storage oscilloscope, and photographed for later analysis. In addition, chart paper recordings of $\dot{V}max$ were obtained using the peak-hold device output.

Fresh stock solutions of drug were prepared for each experiment. Compounds were dissolved in distilled water at total concentrations of 1-10 mg/ml, and subsequently diluted to a final concentration of 3 μM in appropriate volumes of normal Tyrode's solution for evaluation.

Action potential (AP) parameters measured included: diastolic take-off potential (or activation voltage, $V_{act}$); AP overshoot ($V_{os}$); AP duration measured as the time taken to repolarize to −20 mV ($APD_{20}$), −60 mV L($APD_{60}$), and −80 mV ($APD_{80}$); and maximal upstroke velocity ($\dot{V}max$). Data were compared using a two-sample t-test, with statistical significance taken as $p<0.05$. An increase in $APD_{60}$ that occurred without a significant change in $\dot{V}max$ was taken, by definition, to indicate Class III anti-arrhythmic activity.

The data obtained from these experiments establish the compounds of this invention as useful Class III anti-arrhythmic agents.

The compound produced in Example 1 has also been shown to revert sustained atrial flutter induced by rapid electrical stimulation to pure sinus rhythm in dogs (modified inter-caval lesion, Rosenblueth-Garcia-Ramos model) at an i.v. dose of 3 mg/kg. Treatment with lorcainide and procainamide i.v. had not been similarly successful in prior testing of one of these animals. Anesthetized pigs pretreated i.v. with 5 mg/kg of the compound of Example 1 survived both acute ligation and reperfusion of the left anterior descending artery without demonstration of any remarkable ectopic activity, whereas almost 100% of animals similarly treated with standard anti-arrhythmic agents suffer ventricular fibrillation and death.

The structure-Class III activity requirements for these compounds appear to be specific to meta- and para-nitro substitution of the phenyl ring. The orthonitrophenylsulfonamide analogue of the compound of Example 1 exhibited an action potential duration change from control to repolarize dog Purkinje fibers to −60 mV of only 0.1 percent and a maximal upstroke velocity change from control of 4.4 percent, which is clearly not a meaningful Class III activity response. Aliphatic branching of the alkylenediamine such as with 1-isopropylamino-2,2-dimethylethylamine also lowers the Class III activity profile, shifting it towards Class I activity.

Based upon the activity profile elicited by the compounds of this invention in the above-described standard scientifically recognized test models, the compounds are established as anti-arrhythmic agents useful in the treatment of cardiac arrhythmias and conditions characterized by coronary artery occlusion and the resulting myocardial ischemia. For that purpose, the compounds may be administered orally or parenterally in suitable dosage forms compatible with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizer, preservatives and emulsifiers.

The following examples illustrate the preparation of a representative number of compounds of this invention. After each example, the relative score for the compound produced, obtained in the coronary artery ligation experiments and the change in action potential duration and upstroke velocity, where tested, are provided.

EXAMPLE 1

N-(1-Methylethyl)-N-[2-(1-methylethylamino)ethyl]-4-nitrobenzene sulfonamide p-Nitrobenzenesulfonyl chloride (22.1 g, 0.1 mole) in methylene chloride (150 ml) was added dropwise with stirring to N,N'-diisopropyl ethylene diamine (14.4 g, 0.1 mole) and triethylamine (10.1 g, 0.1 mole) in methylene chloride (400 ml). The reaction was stirred one hour at room temperature, washed with water and the solvent removed. The residue dissolved in diethyl ether precipitated the unwanted "bis" byproduct which was filtered and discarded. Chromatography of the filtrate on Dry Column Silica Gel (500 g) with ethyl acetate provided pure product free base as a gum (14.31 g). Conversion, using isopropanol/HCl, to the hydrochloride salt provided the title compound as the hydrochloride salt (14.85 g) m.r. 219°–222° C.

Analysis for: $C_{14}H_{24}N_3O_4SCl$ Calculated: C, 45.96; H, 6.61; N, 11.48. Found: C, 46.53; H, 6.59; N, 11.39.

Score=29

3 $\mu M$, 1000 msec c.l.: % $\Delta APD_{60}$=9.1; % $\Delta \dot{V}max$=15.2.

EXAMPLE 2

N-(1-Methylethyl)-N-[3-(1-methylethylamino)propyl]-4-nitrobenzene sulfonamide

To N,N'-diisopropyl propane-1,3-diamine (23.43 g) in methylene chloride was added p-nitrobenzenesulfonyl chloride (11.08 g, 0.05 mole) dropwise and the reaction stirred 2 hours. The reaction was filtered, stripped, the residue dissolved in diethyl ether, refiltered after washing with water and the contents of the filtrate chromatographed on dry column silica gel with ethyl acetate to provide 9.75 g of clear product as the free base. Preparation of hydrochloride salt gave 8.22 g, m.r. 183°–185° C.

Analysis for: $C_{15}H_{26}ClO_4N_3S$ Calculated: C, 47.42; H, 6.90; N, 11.06. Found: C, 47.77; H, 6.82; N, 10.97.

Score=17

EXAMPLE 3

N-(1-Methylethyl)-N-[2-[(1-methylethyl)amino]ethyl]-3-nitrobenzene sulfonamide

Following the procedure of Example 1, nitrobenzenesulfonyl chloride was reacted with N,N'-diisopropyl ethylene diamine and the product was converted to the hydrochloride salt, m.r. 185°–188° C.

Analysis for: $C_{14}H_{24}ClO_4N_3S$ Calculated: C, 45.96; H, 6.61; N, 11.48. Found: C, 45.86; H, 6.65; N, 11.30.

Score=42

3 $\mu M$, 1000 msec c.l.: % $\Delta APD_{60}$=10.3; % $\Delta \dot{V}_{Max}$=−9.0.

EXAMPLE 4

N-[3-[(1-Methylethyl)amino]propyl]-3-nitrobenzene sulfonamide

Following the procedure of Example 1, m-nitrobenzenesulfonyl chloride was reacted with N-isopropyl propane-1,3-diamine to provide the free base, m.r. 57°–59° C., converted to the hydrochloride salt, m.r. 184°–188° C.

Analysis for: $C_{12}H_{19}N_3O_4S \cdot HCl$ Calculated: C, 42.66; H, 5.97; N, 12.44. Found: C, 42.68; H, 6.05; N, 12.06.

Score=35

3 $\mu M$, 1000 msec c.l.: % $\Delta APD_{60}$=7.6; % $\Delta \dot{V}_{max}$=−5.0.

EXAMPLE 5

N-(1-Methylethyl)-N-[3-[(1-methylethyl)amino]propyl]-3-nitrobenzene sulfonamide

Following the procedure of Example 1, m-nitrobenzenesulfonyl chloride was reacted with N,N-diisopropyl propane-1,3-diamine to obtain the free base which was then converted to the hydrochloride salt, and isolated as white flakes, m.r. 187°–189° C.

Analysis for: $C_{15}H_{25}N_3O_4S \cdot HCl$ Calculated: C, 47.42; H, 6.90; N, 11.06. Found: C, 47.44; H, 6.96; N, 10.89.

Score=30

3 $\mu M$, 1000 msec c.l.: % $\Delta APD_{60}$=5.2; % $\Delta \dot{V}_{max}$=−10.3.

EXAMPLE 6

N-[2-(Diethylamino)ethyl]-N-(1-methylethyl)-4-nitrobenzene sulfonamide p-Nitrobenzene sulfonyl chloride (22.1 g, 0.1 mole) in methylenechloride (200 ml) was added dropwise to N,N-diethylethylene diamine (11.6 g, 0.1 mole) and triethylamine (10.1 g, 0.1 mole) in methylene chloride. The reaction was stirred two days, washed with water, then brine and the solvent removed. The solid residue was dissolved in diethyl ether, filtered through Supercel ®, hexane added and the product obtained by stirring and chilling (18.54 g) m.r. 56°–57° C.

Analysis for: $C_{15}H_{25}N_3O_4S$ Calculated: C, 52.46; H, 7.34; N, 12.23. Found: C, 52.24; H, 7.21; N, 11.89.

Score=26

EXAMPLE 7

N-[2-[(1-methylethyl)amino]ethyl]-4-nitrobenzene sulfonamide

Following the procedure of Example 1, p-nitrobenzenesulfonyl chloride was reacted with N-isopropyl ethylene diamine to provide the crystalline free base, m.r. 143°–145° C. The corresponding hydrochloride salt has m.r. 203°–205° C.

Analysis for: $C_{11}H_{18}N_3O_4SCl$ Calculated: C, 40.80; H, 5.60; N, 12.98. Found: C, 40.91; H, 5.67; N, 12.80.

Score=30

3 $\mu M$, 1000 msec c.l.: % $\Delta APD_{60}$=11.3; % $\Delta \dot{V}max$=4.9

EXAMPLE 8

N-[2-[bis(1-methylethyl)amino]ethyl]-N-(1-methylethyl)-4-nitrobenzenesulfonamide Following the procedure of Example 1, p-nitrobenzenesulfonyl chloride was reacted with N,N',N'-triisopropyl ethylene diamine to obtain the free base as a yellow solid, m.r. 98°–100° C.

Analysis for: $C_{17}H_{29}N_3O_4S$ Calculated: C, 54.96; H, 7.87; N, 11.31. Found: C, 54.43; H, 7.67; N, 11.66.

In an attempt to produce a quaternary ammonium salt, the free base was reacted with allyl bromide in ethanol. The resulting product was the hydrobromide salt of the free base. No evidence of quaternarization of the base was found.

Analysis for: $C_{17}H_{30}N_3O_4SBr$ Calculated: C, 45.12; H, 6.68; N, 9.29. Found: C, 45.24; H, 6.66; N, 9.39.

Score=12

3 μM, 1000 msec c.l.: % $\Delta APD_{60}=29.5$; % $\Delta V max=-1.9$.

EXAMPLE 9

N-[2-[bis(1-methylethyl)amino]ethyl]-4-nitrobenzene sulfonamide

Following the procedure of Example 1, p-nitrobenzenesulfonyl chloride was reacted with N,N-diisopropyl ethylene diamine to give the free base, m.r. 86°-88° C.

Analysis for: $C_{14}H_{23}N_3O_4S$ Calculated: C, 51.05; H, 7.04; N, 12.76. Found: C, 51.34; H, 7.15; N, 12.66.

The hydrochloride salt was prepared by conventional procedues to give a white solid, m.r. 180°-182° C.

Analysis for: $C_{14}H_{23}N_3O_4S \cdot HCl$ Calculated: C, 45.96; H, 6.61; N, 11.48. Found: C, 46.01; H, 6.61; N, 11.50.

3 μM, 1000 msec c.l.:% $\Delta APD_{60}=12.4$; % $\Delta V_{max}=5.9$.

EXAMPLE 10

N-[3-(1-Methylethylamino)propyl]-4-nitrobenzene sulfonamide

Following the procedure of Example 1, p-nitrobenzenesulfonyl chloride was reacted with N-isopropyl propane-1,3-diamine to obtain the free base, which was converted to the hydrochloride salt with isopropanolic HCl and recovered as a white solid with partial solvation, m.r. 230°-232° C.

Analysis for: $C_{12}H_{19}N_3O_4S \cdot HCl \cdot 0.1C_3H_8O$ Calculated: C, 42.96; H, 6.10; N, 12.22. Found: C, 43.25; H, 6.28; N, 12.46.

3 μM, 1000 msec. c.l.: % $\Delta ADP_{60}=1.7$; % $\Delta V max=-10.2$.

What is claimed is:

1. A compound of the formula:

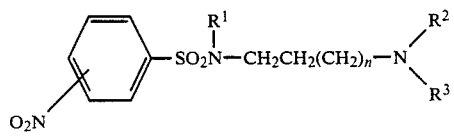

in which the nitro substituent is in 3 or 4 position of the phenyl ring;

$R^1$ is hydrogen or alkyl of 1 to 4 carbon atoms;
$R^2$ is alkyl of 1 to 4 carbon atoms;
$R^3$ is hydrogen or alkyl of 1 to 4 carbon atoms;
and n is one of the integers 0, 1 or 2;
or a pharmaceutically acceptable salt thereof.

2. A compound of claim 1 of the formula:

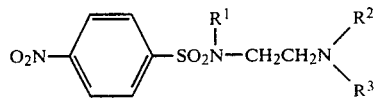

in which
$R^1$ is hydrogen or branched chain alkyl of 3 or 4 carbon atoms;
$R^2$ is branched chain alkyl of 3 or 4 carbon atoms;
$R^3$ is hydrogen or branched chain alkyl of 3 or 4 carbon atoms;
or a pharmaceutically acceptable salt thereof.

3. The compound of claim 1 which is N-(1-methylethyl)-N-[2-(1-methylethylamino)ethyl]-4-nitrobenzene sulfonamide or a pharmaceutically acceptable salt thereof.

4. The compound of claim 1 which is N-(1-methylethyl)-N-[3-(1-methylethylamino)propyl]-4-nitrobenzene sulfonamide or a pharmaceutically acceptable salt thereof.

5. The compound of claim 1 which is N-(1-methylethyl)-N-[2-[(1-methylethyl)amino]ethyl]-3-nitrobenzene sulfonamide or a pharmaceutically acceptable salt thereof.

6. The compound of claim 1 which is N-[3-[(1-methylethyl)amino]propyl]-3-nitrobenzene sulfonamide or a pharmaceutically acceptable salt thereof.

7. The compound of claim 1 which is N-(1-methylethyl)-N-[3-(1-methylethyl)amino]propyl]-3-nitrobenzene sulfonamide or a pharmaceutically acceptable salt thereof.

8. The compound of claim 1 which is N-[2-(diethylamino)ethyl]-N-(1-methylethyl)-4-nitrobenzene sulfonamide or a pharmaceutically acceptable salt thereof.

9. The compound of claim 1 which is N-[2-[(1-methylethyl)amino]ethyl]-4-nitrobenzene sulfonamide or a pharmaceutically acceptable salt thereof.

10. The compound of claim 1 which is N-[2-[bis(1-methylethyl)amino]ethyl]-N-(1-methylethyl)-4-nitrobenzenesulfonamide or a pharmaceutically acceptable salt thereof.

11. The compound of claim 1 which is N-[2-[bis(1-methylethyl)amino]ethyl]-4-nitrobenzene sulfonamide or a pharmaceutically acceptable salt thereof.

12. The compound of claim 1 which is N-[3-(1-methylethylamino)propyl]-4-nitrobenzene sulfonamide or a pharmaceutically acceptable salt thereof.

* * * * *